(12) United States Patent
Yoshida

(10) Patent No.: US 9,307,900 B2
(45) Date of Patent: Apr. 12, 2016

(54) OPHTHALMIC DEVICE, AND METHOD AND PROGRAM FOR CONTROLLING THE SAME

(71) Applicant: CANON KABUSHIKI KAISHA, Tokyo (JP)

(72) Inventor: Hirofumi Yoshida, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 199 days.

(21) Appl. No.: 14/225,237

(22) Filed: Mar. 25, 2014

(65) Prior Publication Data
US 2014/0293227 A1    Oct. 2, 2014

(30) Foreign Application Priority Data
Mar. 27, 2013 (JP) .................................. 2013-066671

(51) Int. Cl.
*A61B 3/10*    (2006.01)
*A61B 3/00*    (2006.01)
*A61B 3/12*    (2006.01)

(52) U.S. Cl.
CPC ............. *A61B 3/0091* (2013.01); *A61B 3/1025* (2013.01); *A61B 3/12* (2013.01)

(58) Field of Classification Search
USPC ......................................... 351/206, 221, 246
See application file for complete search history.

(56) References Cited

U.S. PATENT DOCUMENTS
7,452,081 B2    11/2008 Wiltberger

*Primary Examiner* — Jack Dinh
(74) *Attorney, Agent, or Firm* — Canon U.S.A., Inc., IP Division

(57) ABSTRACT

A light source generates light to fixate a gaze of an eye to be examined, while a scanning unit performs main-scanning and sub-scanning on a fundus of the eye to be examined with the light from the light source.

19 Claims, 6 Drawing Sheets

OPHTHALMIC DEVICE, AND METHOD AND PROGRAM FOR CONTROLLING THE SAME

BACKGROUND

1. Field

Embodiments of the present disclosure relate to an ophthalmic device, and a method and a program for controlling the same.

2. Description of the Related Art

Recently, various ophthalmic devices using optical instruments have been used. The optical instruments for observing an eye include an anterior eye portion photographing machine, a fundus camera, a confocal scanning laser ophthalmoscope (SLO device), and the like. The SLO device is for observing a fundus by emitting light onto the fundus via a scanning optical system and detecting intensity of the light reflected and scattered from the fundus via a confocal optical system.

In such an ophthalmic device, it is expected to observe an eye to be examined accurately by reducing an involuntary eye movement thereof. In an SLO device disclosed in U.S. Pat. No. 7,452,081, when a fundus is scanned with a light source of a fixation lamp by a scanning optical system of the SLO, the light source is switched on and off rapidly, whereby a prescribed pattern of the fixation lamp is projected onto the fundus. Thus, it is possible to fixate a gaze of a subject on the prescribed pattern of the fixation lamp, which pattern is projected onto the fundus, and to reduce an involuntary eye movement of the subject.

SUMMARY

Embodiments of the present disclosure include a light source that generates light to fixate a gaze of an eye to be examined, a scanning unit that performs main-scanning and sub-scanning on a fundus of the eye to be examined with the light from the light source, and a control unit that controls the scanning unit to make a length of an irradiated region in a direction of the sub-scanning equal to or longer than a scanning interval of the main-scanning in the direction of the sub-scanning, wherein the irradiated region in the fundus is irradiated with the light from the light source.

Further features of the present disclosure will become apparent from the following description of exemplary embodiments (with reference to the attached drawings).

DESCRIPTION OF THE EMBODIMENTS

When a device, which emits light of a fixation lamp onto a fundus by scanning the fundus with a light source of the fixation lamp in a conventional manner is used, a gaze of a subject often becomes unstable although an eye to be examined is irradiated with light from the fixation lamp. After a great deal of consideration, the inventors of the present disclosure have discovered a reason why the gaze becomes unstable. The reason is a gap in a direction of sub-scanning between scanning lines of main-scanning during the scanning of the fundus with the light source of the fixation lamp. That is, with such a gap, the light of the fixation lamp is separated into several pieces in the direction of the sub-scanning, whereby the subject becomes uncertain which light of the fixation lamp to look at and thus, the gaze becomes unstable.

It is supposed that a conventional device including a conventional SLO device is to stabilize a gaze by making the light, which is emitted onto the fundus of the eye to be examined from the light source of the fixation lamp, small and by improving luminance of the fixation lamp. However, as a result, the gap is generated and the gaze becomes unstable.

In the view of forgoing, the present embodiments are provided to stabilize the gaze.

Therefore, a length in the direction of the sub-scanning of an irradiated region is made to be equal to or longer than a scanning interval of the main-scanning in the direction of the sub-scanning. The irradiated region is a region where the fundus of the eye to be examined is irradiated with the light from the light source which generates the light to fixate the gaze of the eye to be examined.

As a result, the gap in the direction of the sub-scanning between the scanning lines of the main-scanning can be decreased and the gaze can be stabilized.

In the following, exemplary embodiments will be described with reference to the drawings. Note that in each figure, X indicates a main-scanning direction, Y indicates a sub-scanning direction, and Z indicates a direction orthogonal to the main-scanning direction and the sub-scanning direction.

First Embodiment

In the first embodiment, a fundus imaging device (such as SLO device) will be described as an example of an ophthalmic device.

(Outline of Configuration of Device)

Figure 1:
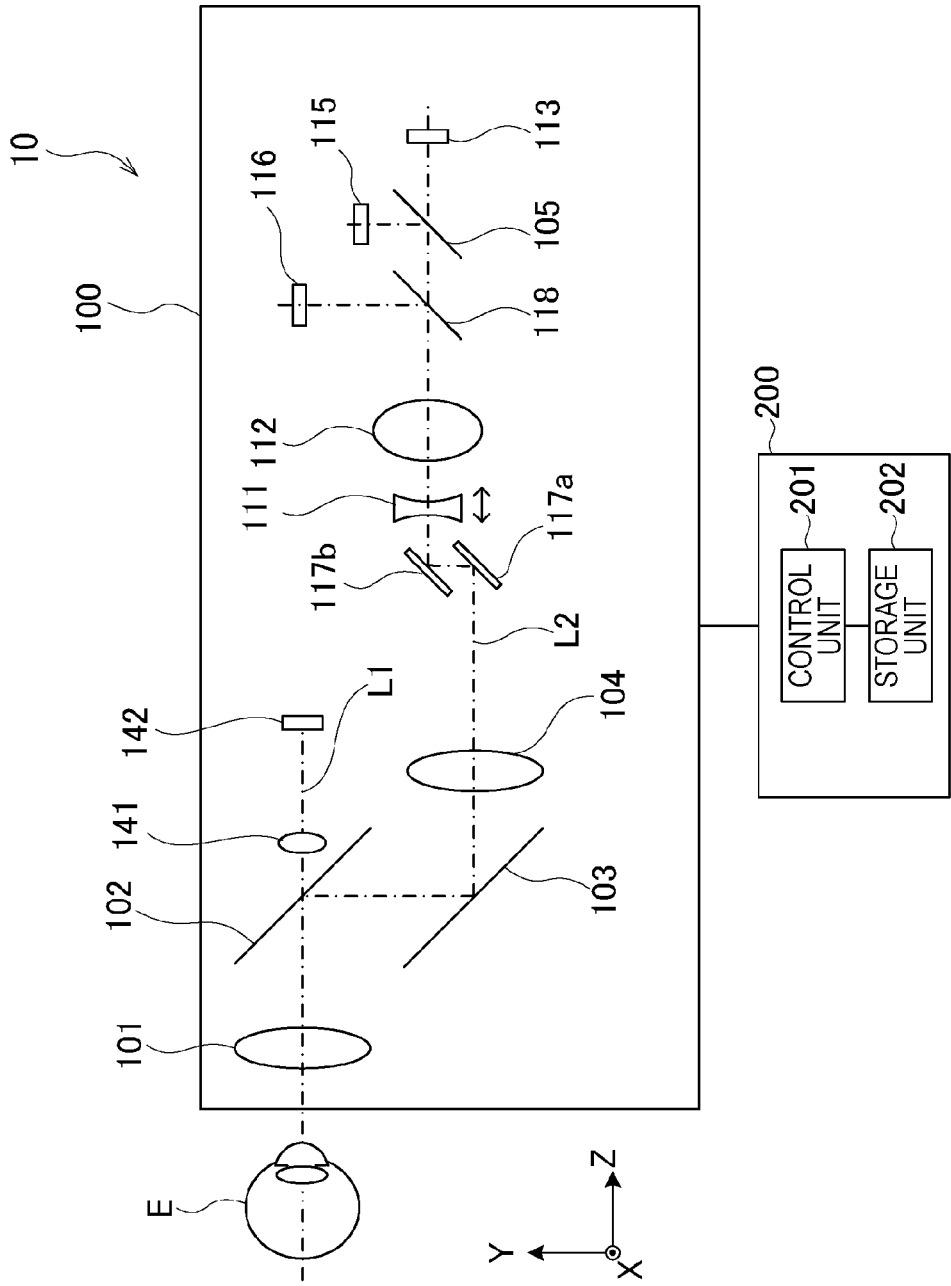
FIG. 1 is a view illustrating a configuration of an ophthalmic device according to a first embodiment.

FIG. 1 is a side view illustrating an example of the fundus imaging device.

The fundus imaging device 10 includes an optical head portion 100 and a control unit portion 200. The optical head portion 100 includes, for example, an optical system for photographing two-dimensional images of an anterior eye and a fundus of an eye to be examined E. The control unit portion 200 controls the optical head portion 100.

(Configuration of Optical Head Portion)

An objective lens 101 opposing the eye to be examined E is arranged in the optical head portion 100. A first dichroic mirror 102, which separates an optical path, is arranged on an optical axis of the objective lens 101. An anterior eye portion observation optical path L1, and a fundus observation optical path and a fixation lamp optical path L2, are separated from each other according to wavelength band ranges thereof, by the first dichroic mirror 102.

A lens 141, and an infrared radiation CCD 142 for observation of the anterior eye are arranged in the optical path L1. The infrared radiation CCD 142 functions as an imaging unit and has a wavelength of illumination light (not illustrated) which is for the observation of the anterior eye. Specifically, the infrared radiation CCD 142 has sensitivity around 970 nm.

In the optical path L2, a mirror 103, a lens 104, a lens 111, a lens 112, and the like are arranged to irradiate the fundus of the eye to be examined with light from a light source 113 of the fixation lamp and a light source 115 which is for the observation of the fundus (for SLO). The mirror 103, the lens 104, the lens 111, the lens 112, and the like are examples of an optical unit.

A focal point of the lens 104 is in the vicinity of a center position of an X scanner 117a and a Y scanner 117b, which will be described in the following. The lens 111 is driven in a direction of the optical axis by a motor (not illustrated). The motor is for a focusing adjustment of the light source 113 of the fixation lamp and the light source 115 which is for the observation of the fundus.

As the light source 113 of the fixation lamp, for example, an LED is used. The light source 113 of the fixation lamp generates the light to fixate the gaze of the eye to be examined E. Also, the light source 115 for the observation of the fundus is an observation light source which generates the light to observe the fundus of the eye to be examined.

In addition, the X scanner 117a and the Y scanner 117b are arranged in the optical path L2. The X scanner 117a and the Y scanner 117b are for scanning the fundus of the eye to be examined E with the light from the light source 113 of the fixation lamp and the light from the light source 115 which is for the observation of the fundus. The X scanner 117a and the Y scanner 117b are examples of a scanning unit which performs main-scanning and sub-scanning with the light from the light source 113 of the fixation lamp and the light from the light source 115 which is for the observation of the fundus. For example, the X scanner 117a, which is an example of a scanning unit for the main-scanning, is formed of a polygon mirror, in order to perform high-speed scanning in the X direction. With such a configuration, the light from the light source 113 of the fixation lamp and the light from the light source 115 which is for the observation of the fundus are applied to the same position on the fundus of the eye to be examined E, via the X scanner 117a and the Y scanner 117b which is an example of a scanning unit for the sub-scanning. Note that the X scanner 117a described above is not limited to the polygon mirror, and may be a resonant mirror, for example.

Also, a prism 118 to which a perforated mirror or a hollow mirror is evaporated is arranged in the optical path L2. Return light from the fundus is separated, by the prism 118, from the light from both of the light source 113 of the fixation lamp and the light source 115 which is for the observation of the fundus. The return light separated by the prism 118 is emitted onto a single detector 116. The single detector 116 is formed of an avalanche photodiode (APD) and is an example of a detecting unit which detects the return light from the fundus. Also, a second dichroic mirror 105 is arranged in a position proximate to the prism 118. By the second dichroic mirror 105, the light from the light source 115 of the SLO and the light from the light source 113 of the fixation lamp are separated from each other according to wavelength band ranges thereof, and emitted onto the eye to be examined E.

(Configuration of Control Unit Portion)

The control unit portion 200 includes a control unit 201, a storage unit 202, and the like. The control unit 201 controls the entire optical head portion 100. Specifically, the control unit 201 controls the light source 113 of the fixation lamp, the light source 115 for the observation of the fundus, the single detector 116, the motor for driving the lens 111, and the like. The storage unit 202 stores, for example, a program to be executed by the control unit 201.

Figure 2A:
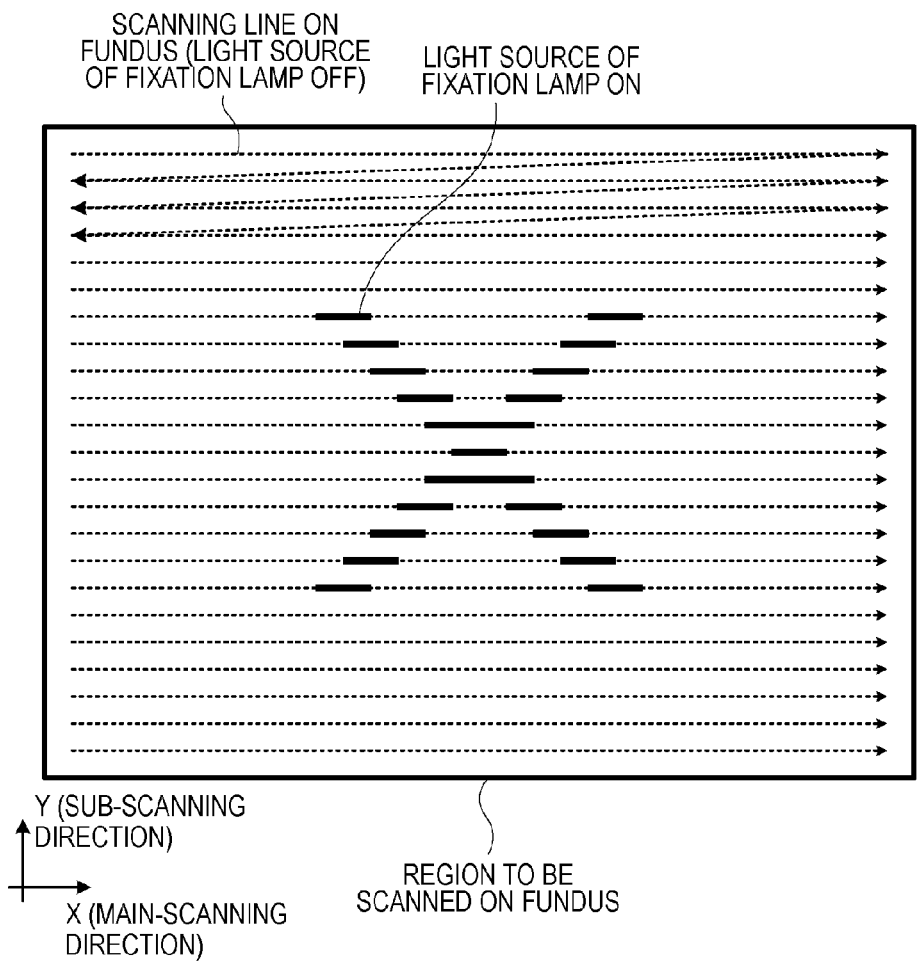
FIGS. 2A and 2B are views illustrating scanning of a fundus with a light source of a fixation lamp.
Figure 2B:
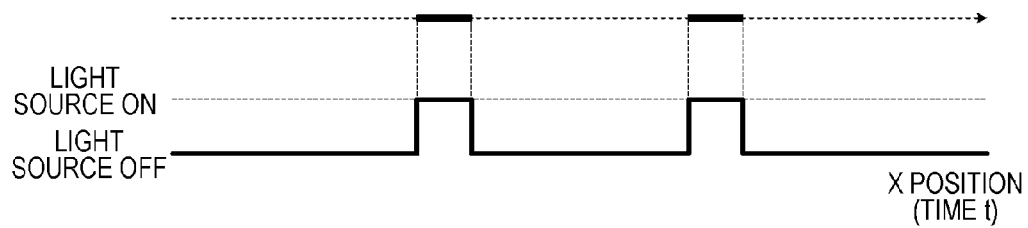

Then, a case of scanning the fundus with the light from the light source 113 of the fixation lamp will be described with reference to FIGS. 2A and 2B. FIG. 2A is a view illustrating a state in which scanning is performed with the light source 113 of the fixation lamp. FIG. 2B is a view illustrating timing of turning on and off the light source 113.

As illustrated in FIG. 2A, first, the X scanner 122a scans a region to be scanned on the fundus in the X direction, that is, in the direction of the main-scanning (main-scanning direction), with the light source 113 of the fixation lamp (see dashed line). When the scanning in the main-scanning direction is finished, the Y scanner 122b serially moves a scanning line of the light source 113 of the fixation lamp in the Y direction, that is, in the direction of the sub-scanning (sub-scanning direction). Then, the X scanner 122a scans again in the main-scanning direction with the light source 113 of the fixation lamp. Thus, the entire region to be scanned is scanned. That is, the control unit 201 controls the light source 113 to be turned on and off, according to positions of the main-scanning and the sub-scanning.

As illustrated in FIG. 2B, when the scanning in the main-scanning direction is performed with the light source 113 of the fixation lamp, the light source 113 is turned on at a prescribed position in a prescribed distance. In other positions, the light source 113 is turned off. The light source 113 is turned on and off by the control unit 201. By controlling on and off of the light source 113 of the fixation lamp, the control unit 201 can project a prescribed pattern of the fixation lamp, which is formed by the light from the light source 113, onto the fundus of the eye to be examined E. In FIG. 2A, "x" is illustrated as an example of a prescribed pattern of a fixation lamp.

The fundus imaging device 10 can obtain an image of the fundus by detecting the return light with the single detector 116. The return light is light, from the light source 115 which is for the observation of the fundus, emitted onto and reflected from the fundus while a gaze of a subject is fixated on the fixation lamp.

Figure 3A:
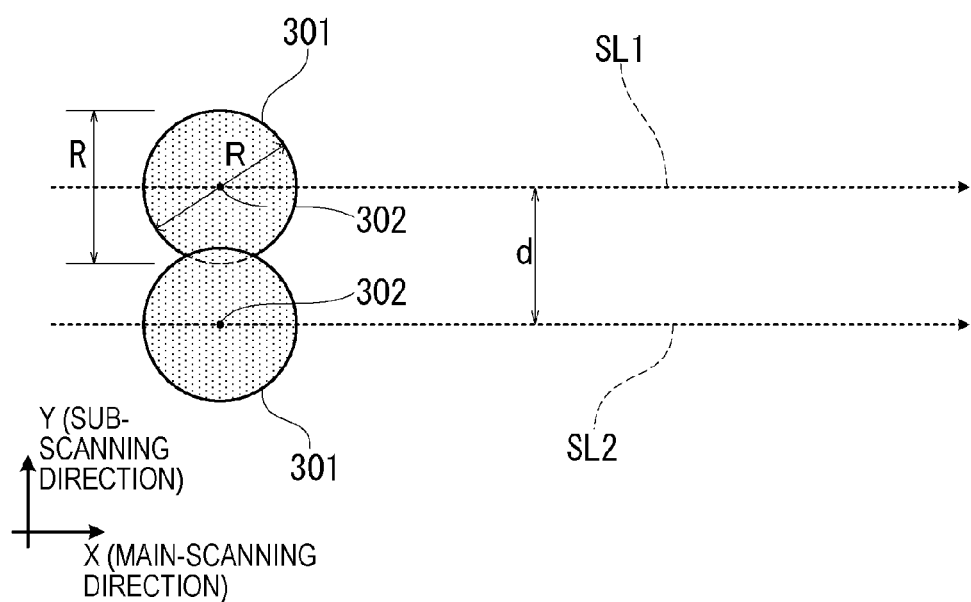
FIGS. 3A and 3B are views illustrating a positional relationship, on the fundus, between optical images of the light source of the fixation lamp.
Figure 3B:
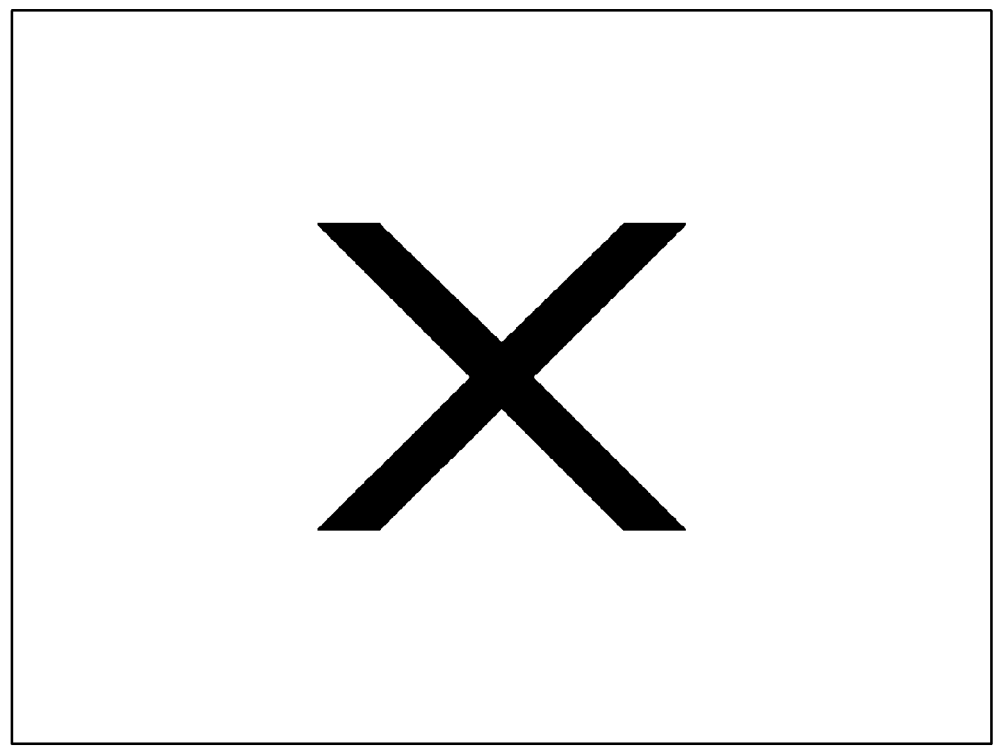

Here, when a gap is generated, in the fixation lamp for fixating the gaze, in the direction of the sub-scanning between scanning lines of the main-scanning, the gaze of the eye to be examined E cannot be stabilized. Thus, in the present embodiment, the length in the sub-scanning direction of the light emitted onto the fundus from the light source 113 is set to be equal to or longer than a scanning interval of the main-scanning in the direction of the sub-scanning. In the following, details will be described with reference to FIGS. 3A and 3B. FIG. 3A is a view illustrating the light emitted onto the fundus from the light source 113 in each main-scanning direction, that is, an optical image (irradiated region) from the light source 113, which image is formed on the fundus. FIG. 3B is a view illustrating an example of a pattern, which is projected onto the fundus, of a fixation lamp.

In the present embodiment, as illustrated in FIG. 3A, an image 301 on the fundus from the light source 113 is a circular shape of R in diameter. The image 301 from the light source is applied with its center point 302 being moved along a scanning line SL1 in the main-scanning direction. Here, as illustrated in FIG. 3A, a scanning interval, in the sub-scanning direction, between the scanning line SL1 in the main-scanning direction and a scanning line SL2 in the main-scanning direction is d. Thus, the images 301 are applied with the scanning interval d between the center points 302 thereof.

As described above, in the present embodiment, the length in the sub-scanning direction (here, diameter R) of the image 301 on the fundus from the light source 113 is set to be equal to or longer than the scanning interval in the direction of the sub-scanning between the main-scanning lines (equal to or longer than scanning interval d).

That is, the size of the image 301 from the light source is set to satisfy the following equation:

$$d \leq R \qquad (1)$$

The value R changes when the lens 111 is driven, and thus, it is preferable to use the smallest diameter, which is a diameter when the lens 111 is driven, as the value R. Also, the value d changes depending on an axial length of the eye to be examined, and thus, it is preferable to use a scanning interval in the case where the axial length is long, as the value d.

Note that, if a diameter of a light emitter of the light source 113 is r and a factor from the light source 113 to the fundus of the eye to be examined E in FIG. 1 is β, R=|β×r|. Thus, $$d \leq |\beta \times r| \qquad (2)$$

By designing an optical system and setting the size of a light emitting region of the light source 113 to satisfy the relationship described above, a gap in the sub-scanning direction is not generated between the image 301 applied on the scanning line SL1 from the light source and the image 301 applied on the scanning line SL2 from the light source. Thus, by using such images 301 from the light source to irradiate the fundus with light from the fixation lamp, as illustrated in FIG. 3B, a gap generated, in the direction of the sub-scanning, between the scanning lines of the main-scanning can be degreased. As a result, it becomes possible to stabilize the gaze of the eye to be examined E and to obtain a good image of the fundus.

Note that, by increasing the diameter R of the image 301 on the fundus from the light source, integral time of the light on the fundus becomes shorter in a boundary portion of the fixation lamp. As a result, apparent luminance becomes lower in the boundary portion, and the boundary portion tends to become unclear. Thus, in the present embodiment, the quantity of light, which is emitted onto the fundus from the light source 113 in the boundary portion, is increased to make the apparent light quantity constant and the boundary portion clear.

In the following, processing to make the boundary portion clear will be described in detail with reference to FIGS. 4A and 4B.

Figure 4A:
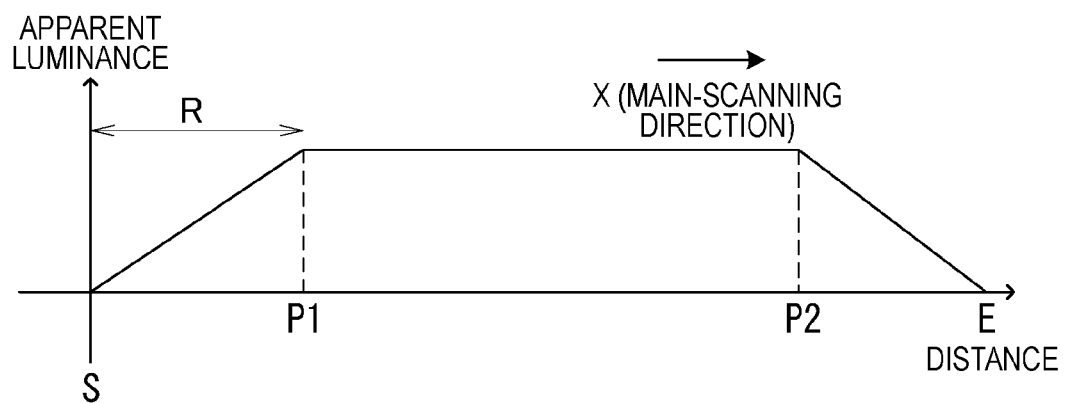
FIGS. 4A and 4B are views illustrating a relationship between the light source and luminance when the fundus is scanned with the light source of the fixation lamp.

FIG. 4A is a view illustrating the apparent luminance on the fundus when the fundus is scanned, along the scanning line in the main-scanning direction, with the light source 113 of the constant quantity of light. Here, a position S indicates a lighting position where the light source 113 transitions from an unlit state to a lighting state. A position E indicates an unlit position where the light source 113 transitions from the lighting state to the unlit state.

As illustrated in FIG. 4A, when the fundus is scanned with the light source 113 from the position S to a position P1 which corresponds to the diameter R of the light source 113, the apparent luminance monotonically increases. Beyond the position P1, the apparent luminance becomes constant. Also, as illustrated in FIG. 4A, the apparent luminance monotonically decreases from a position P2 to the position E which is a position to turn off the light source 113. The position P2 is away from the position E to the side of the position S, for the length of the diameter R of the light source 113. The regions in which the apparent luminance monotonically increases and decreases are the regions where the boundary portion becomes unclear.

Figure 4B:
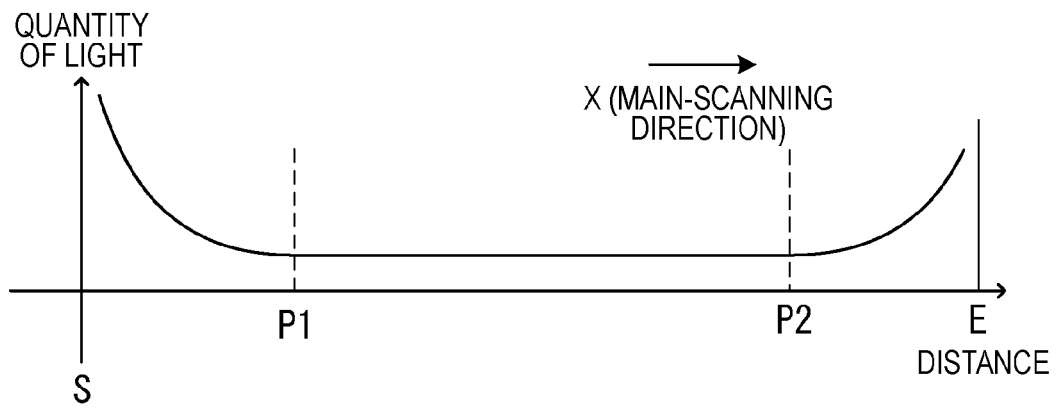

FIG. 4B is a view illustrating change in the quantity of light which is emitted from the light source 113 to make the boundary portion clear. In FIG. 4B, a relationship between the luminance and the distance illustrated in FIG. 4A is inversed.

Figure 5A:
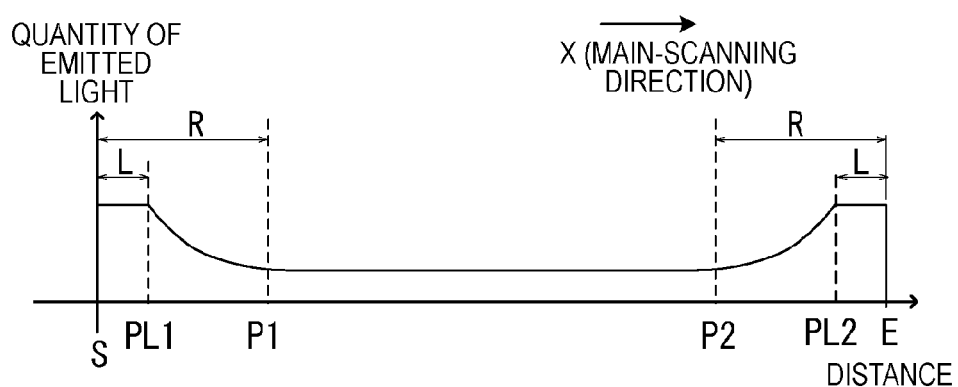
FIGS. 5A and 5B are views illustrating change in the quantity of light when the fundus is scanned with the light source of the fixation lamp.

As illustrated in FIG. 4B, by controlling the quantity of light emitted from the light source 113, the apparent luminance on the fundus can be made constant. Note that in FIG. 4B, a left end and a right end diffuse infinitely. Thus, actually, as illustrated in FIG. 5A, the quantity of light is controlled to be constant between the position S and a position PL1 which is away from the position S for a prescribed distance L, and between the position E and a position PL2 which is away from the position E for the distance L. That is, the control unit 201 preferably controls the light source 113 to change the quantity of light which is emitted onto the fundus of the eye to be examined while the light source 113 is in the lighting state (not only to turn on and off the light source 113), according to a position of the main-scanning and a position of the sub-scanning. In addition, while the light source 113 is in the lighting state, it is preferable to control the light source 113, by the control unit 201, to make the quantity of light, which is emitted onto the fundus of the eye to be examined in an early period and a late period of lighting of the light source 113, greater than that in a middle period of lighting of the light source 113. Note that the early period of lighting of the light source 113 is, for example, a period in which the main-scanning is performed from the position S to the position P1. Also, the middle period of lighting of the light source 113 is, for example, a period in which the main-scanning is performed from the position P1 to the position P2. The late period of lighting of the light source 113 is, for example, a period in which the main-scanning is performed from the position P2 to the position E.

As illustrated in FIG. 5A, the control unit 201 makes the quantity of light from the light source 113 in the position S greater than the quantity of light from the light source 113 which is in the lighting state and away from the position S for a prescribed distance (for example, the light source in the position P1). Here, the prescribed distance is a length in the main-scanning direction of the light source 113, that is, the diameter R of the image from the light source 113. Also, the control unit 201 controls the quantity of light from the light source 113 to be gradually smaller as the scanning is performed from the position PL1 to the position P1.

In addition, as illustrated in FIG. 5A, the control unit 201 makes the quantity of light from the light source 113 in the position E greater than the quantity of light from the light source 113 which is in the lighting state and away from the position E for a prescribed distance (for example, the light source in the position P2). Here, the prescribed distance is a length in the main-scanning direction of the light source 113, that is, the diameter R of the image from the light source 113. Also, the control unit 201 controls the quantity of light from the light source 113 to be gradually greater as the scanning is performed from the position P2 to the position PL2.

Figure 5B:
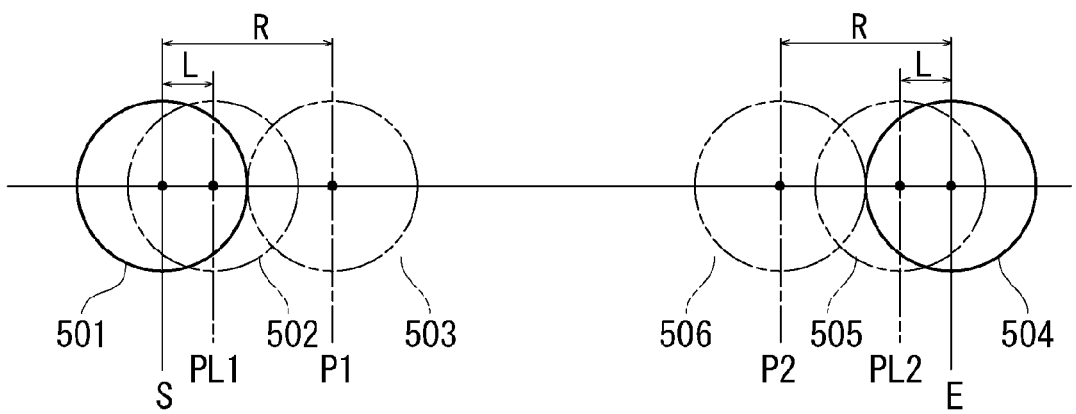

FIG. 5B indicates images projected onto the fundus from the light source 113 according to FIG. 5A, from the moment when the light source 113 is turned on to the moment immediately before the light source 113 is turned off. In FIG. 5B, an image 501 at the position S is an image during a transition, that is, when the light source 113 transitions from the unlit state to the lighting state. An image 502 at the position PL1 is an image applied in the main-scanning direction from the position S for the distance L. An image 503 at the position P1 is an image applied in the main-scanning direction from the position S for the distance R, the image 503 being the image after the transition of the light source 113 to the lighting state. Here, luminance of the image 501 and that of the image 502 are the same and greater than that of the image 503.

Also, an image 504 at the position E is an image immediately before the light source transitions from the lighting state to the unlit state. An image 505 at the position PL2 is an image which is away from the position E for the distance L. An image 506 at the position P2 is an image which is away from the position E for the distance R. Here, luminance of the image 504 and that of the image 505 are the same and greater than that of the image 506.

Note that the position P1 and the position P2 correspond to the prescribed positions. Also, the distance L is preferably set as a distance which a subject cannot recognize visually (for example, equal to or shorter than 30 µm).

By controlling the quantity of light from the light source 113 in this manner, the apparent luminance can be made substantially constant in the boundary portion of the fixation lamp, whereby the boundary portion of the fixation lamp can be made clear and the gaze of the eye to be examined can be further stabilized.

Note that, in the present embodiment, configuration is not limited to what has been described above. A pinhole (not illustrated) can be arranged on the side of the optical path of the light source 113 of the fixation lamp, and the fundus can be scanned with an image of the pinhole. In that case, the image of the pinhole is "the image on the fundus from the light source 113" in FIG. 3A.

Also, in the present embodiment, the shape of the light source 113 has been described as a circular shape but may be a quadrangular shape. In addition, when a pattern of the fixation lamp is "x" like the present embodiment, the shape of the light source 113 may be an aslant quadrangular shape which is along the edge of "x". It is possible to form two quadrangular-shaped pinholes "\" and "/" with two light sources and to project "x" by switching illumination of the two pinholes "\" and "/".

Also, in the present embodiment, a case of controlling the quantity of light from the light source 113 by the control unit 201 to make the boundary portion of the fixation lamp clear has been described, but the present embodiment is not limited to the case. For example, a variable neutral density filter (ND filter) which is controlled by the control unit 201 may be arranged between the second dichroic mirror 105 and the light source 113 of the fixation lamp which are illustrated in FIG. 1. In this case, a relationship between the neutral density filter and the quantity of light emitted onto the fundus is measured in advance. Then, the control unit 201 controls the neutral density filter based on the measured relationship, while keeping the quantity of light from the light source 113 constant. Thus, as illustrated in FIG. 5A, the quantity of light emitted onto the fundus can be increased and decreased and the boundary portion of the fixation lamp can be made clear.

Second Embodiment

The second embodiment is an ophthalmic device 20 in which an OCT device is added to the fundus imaging device 10 of the first embodiment. The OCT device functions as a tomographic image obtaining unit which obtains a tomographic image of an eye to be examined.

(Outline of Configuration of Device)

Figure 6:
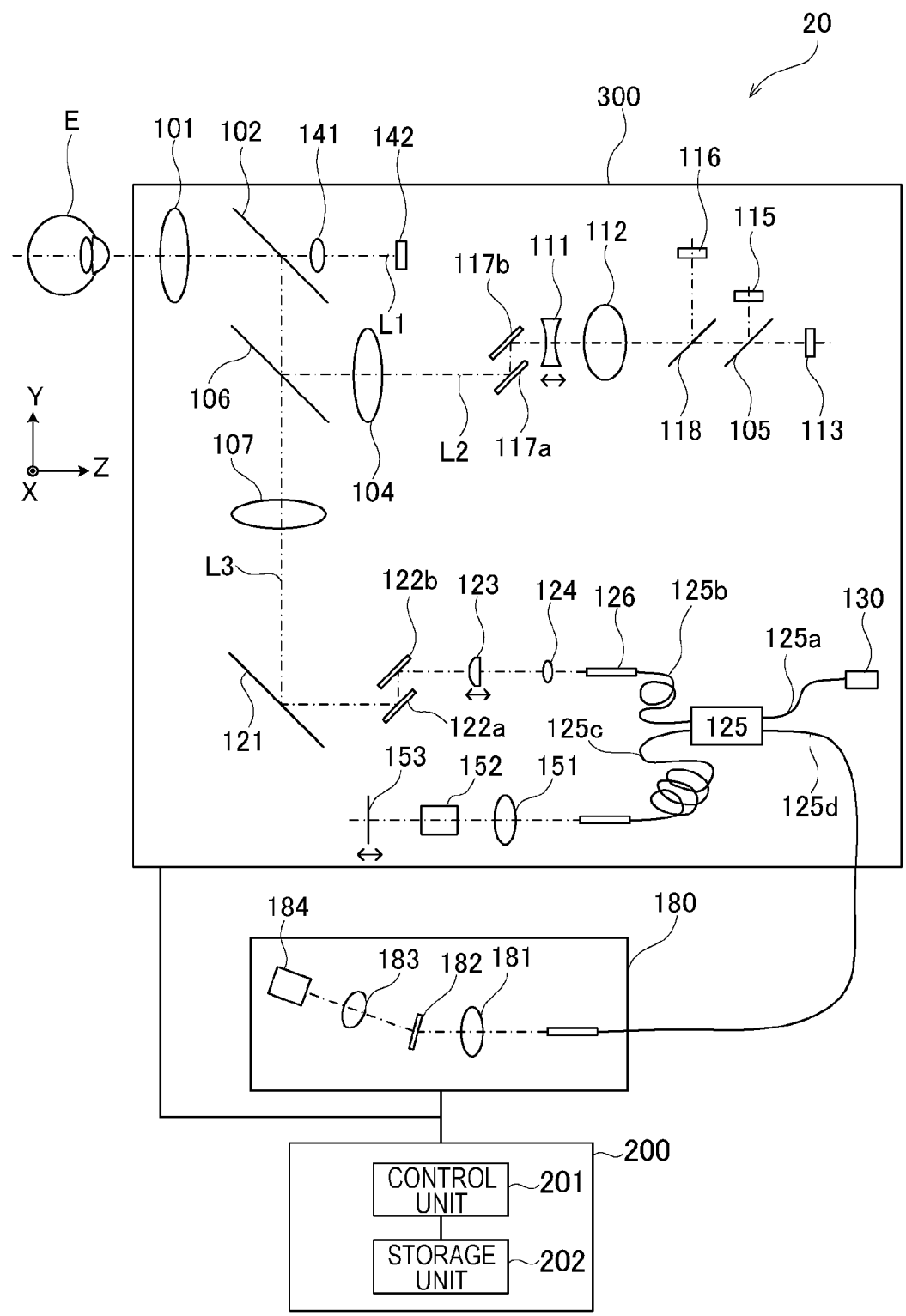
FIG. 6 is a view illustrating a configuration of an ophthalmic device according to a second embodiment.

FIG. 6 is a side view illustrating an example of the ophthalmic device 20.

The ophthalmic device 20 includes an optical head portion 300, a control unit portion 200, and a spectroscope 180. In the present embodiment, an optical path L1 and an optical path L2 are similar to those of the first embodiment, and a position of an image projected onto a fundus from a light source 113 of a fixation lamp and control of the quantity of light are also similar to those of the first embodiment, and thus, description thereof is omitted. Also, in the optical head portion 300 and the control unit portion 200, the same reference signs are given to components which are similar to those of the first embodiment and description thereof is omitted.

(Optical Head Portion and Optical System of Spectroscope)

In the first embodiment, the mirror 103 is arranged between the first dichroic mirror 102 and the lens 104, but in the present embodiment, a third dichroic mirror 106 is arranged therebetween, as illustrated in FIG. 6. The third dichroic mirror 106 separates the optical path L2 and an optical path L3 from each other, according to wavelength band ranges thereof. The optical path L2 is for obtaining a two-dimensional image of a fundus and the optical path L3 is for obtaining a tomographic image of the fundus.

The optical path L3 forms an optical system (OCT optical system) to obtain the tomographic image. The optical path L3 is for imaging the tomographic image of the fundus of the eye to be examined E and specifically for obtaining an interfering signal to form the tomographic image.

In the optical path L3, a lens 107, a mirror 121, an X scanner 122a, and a Y scanner 122b are arranged. The X scanner 122a and the Y scanner 122b function as measurement light deflection units to scan the fundus of the eye to be examined E with light. Also, a measurement light source 126 is a light source of measurement light and makes the measurement light enter a measurement optical path. Here, the measurement light source 126 is a fiber end and conjugated optically with the fundus portion of the eye to be examined E. A lens 123 and a lens 124 are arranged between the measurement light source 126, and the X scanner 122a and the Y scanner 122b. The lens 123 is an example of a focusing adjustment unit and driven by a motor (not illustrated) to perform a focusing adjustment. The focusing adjustment is performed to form an image on the fundus of the eye to be examined E with the light emitted from the measurement light source 126 which is the fiber end. By the focusing adjustment, an image from the measurement light source 126 can be formed on the fundus of the eye to be examined E and return light from the fundus of the eye to be examined E can be effectively returned to an optical fiber 125b via the measurement light source 126.

Note that in FIG. 6, an optical path between the X scanner 122a and the Y scanner 122b are formed on a plane of paper, but actually, the optical path is formed vertically to the plane of paper.

Next, configurations of an optical path from a light source 130, a reference optical system, and the spectroscope will be described.

In FIG. 6, the ophthalmic device 20 includes the light source 130, a mirror 153, a dispersion compensate glass 152, an optical coupler 125, single-mode optical fibers 125a to 125d which are connected to and integrated with the optical coupler, a lens 151, and the spectroscope 180.

With this configuration, a Michelson interferometer is formed. The light emitted from the light source 130 is separated into measurement light on the side of the optical fiber 125b and reference light on the side of the optical fiber 125c, through the optical fiber 125a and via the optical coupler 125. The measurement light is emitted onto the fundus of the eye to be examined E, which is an object to be observed, through the optical path L3 of the OCT optical system described above. Then, the measurement light is reflected and scattered from a retina and reaches the optical coupler 125 through the same optical path.

Meanwhile, the reference light reaches the mirror 153 via the optical fiber 125c, the lens 151, and the dispersion compensate glass 152 and is reflected by the mirror 153, the dispersion compensate glass 152 being inserted to correct dispersion of the measurement light and the reference light. Then, the reference light returns in the same optical path and reaches the optical coupler 125.

By the optical coupler 125, the measurement light and the reference light are combined and become interfering light (combined light). Here, when the length of the optical path of the measurement light and the length of the optical path of the reference light become substantially the same, interference occurs. The mirror 153 is held adjustably in the direction of the optical axis by a motor and a driving mechanism (not illustrated). The mirror 153 can adjust the length of the optical path of the reference light to the length of the optical path of the measurement light which changes depending on the eye to be examined E. The interfering light is led to the spectroscope 180 via the optical fiber 125d.

The spectroscope 180 includes a lens 181, a diffraction grating 182, a lens 183, and a line sensor 184. After becoming substantially parallel light via the lens 181, the interfering light emitted from the optical fiber 125d is dispersed by the diffraction grating 182 and made to form an image on the line sensor 184 by the lens 183.

Next, surroundings of the light source 130 will be described. The light source 130 is a super luminescent diode (SLD) which is a typical low-coherent light source. The center wavelength is 855 nm and the width of a wavelength band is about 100 nm. Here, the width of the band affects resolution in a direction of an optical axis of the obtained tomographic image, and thus, the width of the band is an important parameter. Here, the SLD is selected as the light source, but the light source may be any kind as long as low-coherent light can be emitted. Thus, for example, an amplified spontaneous emission (ASE) light source may also be used. Considering that the light source is used to measure an eye, the center wavelength of near-infrared light is suitable for the light source. Also, the center wavelength affects resolution in the lateral direction of the obtained tomographic image, and thus, the center wavelength is preferably as short as possible. For the two reasons above, the center wavelength is set to be 855 nm.

In the present embodiment, the Michelson interferometer is used as an interferometer, but a Mach-Zehnder interferometer may be used instead. It is preferable to select an interferometer according to a difference in the quantity of light between the measurement light and the reference light. When the difference is large, the Mach-Zehnder interferometer is preferably used. When the difference is relatively small, the Michelson interferometer is preferably used. In this manner, according to the present embodiment, a tomographic image of an eye to be examined can be obtained.

In the above, various exemplary embodiments have been described. These exemplary embodiments are not seen to be limiting and various modifications can be made within the scope of the present disclosure.

Other Embodiments

Additional embodiments can also be realized by a computer of a system or apparatus that reads out and executes computer executable instructions recorded on a storage medium (e.g., computer-readable storage medium) to perform the functions of one or more of the above-described embodiment(s), and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™, a flash memory device, a memory card, and the like.

While the present disclosure has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-066671, filed Mar. 27, 2013, which is hereby incorporated by reference herein in its entirety.

What is claimed is:

1. An ophthalmic device comprising:
   a light source configured to generate light to fixate a gaze of an eye to be examined;
   a scanning unit configured to perform main-scanning and sub-scanning on a fundus of the eye to be examined with the light from the light source; and
   a control unit configured to control the scanning unit in order to make a length of an irradiated region in a direction of the sub-scanning equal to or longer than a scanning interval of the main-scanning in the direction of the sub-scanning, wherein the irradiated region in the fundus is irradiated with the light from the light source.

2. The ophthalmic device according to claim 1, wherein while the light source is turned on and off by the control unit according to a position of the main-scanning and a position of the sub-scanning, the scanning unit performs the main-scanning and the sub-scanning on the fundus of the eye to be examined with the light from the light source, whereby a prescribed pattern of a fixation lamp is projected onto the fundus of the eye to be examined.

3. The ophthalmic device according to claim 1, wherein the control unit controls the light source, according to a position of the main-scanning and a position of the sub-scanning, to turn the light source on and off and to change a quantity of light emitted onto the fundus of the eye to be examined when the light source is in a lighting state.

4. The ophthalmic device according to claim 3, wherein the control unit increases and decreases the quantity of light emitted onto the fundus of the eye to be examined by adjusting the quantity of light of the light source.

5. The ophthalmic device according to claim 3, further comprising a light dimming unit configured to dim the light from the light source,
   wherein the control unit increases and decreases the quantity of light emitted onto the fundus of the eye to be examined by controlling the light dimming unit.

6. The ophthalmic device according to claim 1, wherein when the light source is in a lighting state, the control unit controls the light source in order to make a quantity of light emitted onto the fundus of the eye to be examined in an early period and a late period of lighting of the light source greater than that in a middle period of lighting of the light source.

7. The ophthalmic device according to claim 6, wherein the prescribed distance is a length in a direction of the main-scanning of an irradiated region in which the fundus is irradiated with the light from the light source.

8. The ophthalmic device according to claim 1, wherein the control unit controls the light source in order to make a quantity of light emitted onto the fundus of the eye to be examined during a transition of the light source from an unlit state to a lighting state greater than that in the lighting state after the transition.

9. The ophthalmic device according to claim 1, wherein the control unit makes a quantity of light emitted onto the fundus of the eye to be examined gradually smaller, when the light source is turned on and the light from the light source is applied, by the scanning unit, on the fundus of the eye to be examined from a lighting position, which is irradiated with the light from the light source, to a specific position that is away from the lighting position for a prescribed distance in a direction of the main-scanning.

10. The ophthalmic device according to claim 1, wherein the control unit controls the light source to make a quantity of light emitted onto the fundus of the eye to be examined immediately before the light source transitions from a lighting state to an unlit state, greater than that in the lighting state that is prior to immediately before the light source transitions from the lighting state to the unlit state.

11. The ophthalmic device according to claim 1, wherein the control unit gradually increases a quantity of light emitted onto the fundus of the eye to be examined, when the light from the light source is applied, by the scanning unit, from a specific position to an unlit position which is away from the specific position for a prescribed distance in a direction of the main-scanning, while the light source is turned on and the fundus of the eye to be examined is irradiated with the light from the light source.

12. The ophthalmic device according to claim 1, further comprising an observation light source configured to generate light to observe the eye to be examined, and
a detecting unit configured to detect return light which is light, from the observation light source, emitted onto and reflected from the eye to be examined,
wherein the scanning unit performs the main-scanning and the sub-scanning on the fundus of the eye to be examined with the light from the observation light source and the light from the light source.

13. The ophthalmic device according to claim 1, further comprising a tomographic image obtaining unit configured to obtain a tomographic image of the eye to be examined, based on combined light in which return light from the eye to be examined, which eye is irradiated with measurement light, and reference light corresponding to the measurement light are combined.

14. The ophthalmic device according to claim 1, wherein the scanning unit includes:
a scanning unit configured to perform the main-scanning, and
a scanning unit configured to perform the sub-scanning.

15. An ophthalmic device comprising:
a light source configured to generate light to fixate a gaze of an eye to be examined;
a scanning unit configured to perform main-scanning and sub-scanning on a fundus of the eye to be examined with the light from the light source; and
a control unit configured to control the light source, according to a position of the main-scanning and a position of the sub-scanning, to turn the light source on and off and to change the quantity of light emitted onto the fundus of the eye to be examined when the light source is in a lighting state.

16. A method for controlling an ophthalmic device comprising:
generating light to fixate a gaze of an eye to be examined; and
performing main-scanning and sub-scanning on a fundus of the eye to be examined with the light,
wherein a length in a direction of the sub-scanning of an irradiated region, in which the fundus is irradiated with the light, is made equal to or longer than a scanning interval of the main-scanning in the direction of the sub-scanning.

17. A non-transitory computer-readable storage medium storing computer executable instructions for causing a computer to execute the method for controlling an ophthalmic device according to claim 16.

18. A method for controlling an ophthalmic device comprising:
generating light to fixate a gaze of an eye to be examined; and
performing main-scanning and sub-scanning on a fundus of the eye to be examined with the light:
turning, according to a position of the main-scanning and a position of the sub-scanning, the light on and off and changing the quantity of light emitted onto the fundus of the eye to be examined.

19. A non-transitory computer-readable storage medium storing a program for causing a computer to execute the method for controlling an ophthalmic device according to claim 18.

* * * * *